(12) United States Patent
Velmahos et al.

(10) Patent No.: US 10,064,695 B2
(45) Date of Patent: Sep. 4, 2018

(54) SYSTEMS FOR ABDOMINAL WALL LIFTING AND NEEDLE INSERTION

(71) Applicants: George Velmahos, Boston, MA (US);
Gabriel Gruionu, Somervile, MA (US);
Lucian Gheorghe Gruionu, Craiova (RO)

(72) Inventors: George Velmahos, Boston, MA (US);
Gabriel Gruionu, Somervile, MA (US);
Lucian Gheorghe Gruionu, Craiova (RO)

(73) Assignee: The General Hospital Corporation, Boston, MA (US)

(*) Notice: Subject to any disclaimer, the term of this patent is extended or adjusted under 35 U.S.C. 154(b) by 364 days.

(21) Appl. No.: 14/770,338

(22) PCT Filed: Feb. 26, 2014

(86) PCT No.: PCT/US2014/018621
§ 371 (c)(1),
(2) Date: Aug. 25, 2015

(87) PCT Pub. No.: WO2014/134140
PCT Pub. Date: Sep. 4, 2014

(65) Prior Publication Data
US 2016/0008075 A1    Jan. 14, 2016

Related U.S. Application Data

(60) Provisional application No. 61/769,231, filed on Feb. 26, 2013.

(51) Int. Cl.
*A61B 90/11* (2016.01)
*A61M 13/00* (2006.01)
(Continued)

(52) U.S. Cl.
CPC .......... *A61B 90/11* (2016.02); *A61B 17/3403* (2013.01); *A61B 17/3474* (2013.01);
(Continued)

(58) Field of Classification Search
CPC ........ A61B 17/3403; A61B 2017/3413; A61B 10/0233; A61B 17/3478; A61B 90/11;
(Continued)

(56) References Cited

U.S. PATENT DOCUMENTS 5,236,417 A * 8/1993 Wallis ................... A61M 25/00
600/432
5,269,754 A * 12/1993 Rydell ............... A61B 17/3403
604/159

(Continued)

OTHER PUBLICATIONS

Ahmad, et al., Laparoscopic Entry Techniques (Review), Prepared and Maintained by The Cochrane Collaboration, Published in The Cochrane Library, 2008, Issue 2, 27 pages.
(Continued)

*Primary Examiner* — Theodore Stigell
(74) *Attorney, Agent, or Firm* — Quarles & Brady LLP (57) ABSTRACT

A system and method for coordinated and controlled abdominal gas insufflation includes clamp configured to engage an abdominal wall. A needle advancement control is configured to receive a needle and advance the needle toward the clamp to extend into a portion of the abdomen. A feedback device is configured to monitor the needle as it is advanced into the portion of the abdomen of the subject and provide feedback indicating that the needle has pierced the portion the abdomen.

25 Claims, 8 Drawing Sheets

(51) Int. Cl.
*A61B 17/34* (2006.01)
*A61B 17/00* (2006.01)
*A61B 17/28* (2006.01)
*A61B 8/12* (2006.01)
*A61B 90/00* (2016.01)

(52) U.S. Cl.
CPC .............. *A61M 13/003* (2013.01); *A61B 8/12* (2013.01); *A61B 2017/00106* (2013.01); *A61B 2017/00115* (2013.01); *A61B 2017/00128* (2013.01); *A61B 2017/2808* (2013.01); *A61B 2017/3407* (2013.01); *A61B 2017/3409* (2013.01); *A61B 2017/3413* (2013.01); *A61B 2090/066* (2016.02); *A61M 2202/0225* (2013.01); *A61M 2205/3334* (2013.01); *A61M 2205/8206* (2013.01)

(58) Field of Classification Search
CPC ........ A61B 2090/062; A61B 17/22031; A61B 17/29; A61B 17/3474; A61B 17/02; A61M 5/427; A61M 13/003
USPC .... 606/1, 130, 167, 169, 205–207; 600/218, 600/219
See application file for complete search history.

(56) References Cited

U.S. PATENT DOCUMENTS

| | | | | |
|---|---|---|---|---|
| 5,374,252 A | * | 12/1994 | Banks ................ | A61B 17/3496 600/567 |
| 5,449,365 A | * | 9/1995 | Green ................ | A61B 17/1285 227/901 |
| 5,882,302 A | * | 3/1999 | Driscoll, Jr. ........... | A61B 5/416 600/371 |
| 6,402,714 B1 | * | 6/2002 | Kraft-Kivikoski ......................... | A61M 13/003 600/560 |
| 6,899,721 B2 | * | 5/2005 | Sferco .................... | A61B 6/481 600/420 |
| 7,226,450 B2 | * | 6/2007 | Athanasiou ........ | A61B 10/0233 604/154 |
| 8,224,327 B2 | * | 7/2012 | Suh ................... | H04W 36/0033 455/436 |
| 8,244,327 B2 | | 8/2012 | Fichtinger et al. | |
| 2005/0197620 A1 | * | 9/2005 | Tu ...................... | A61B 17/3417 604/26 |
| 2012/0197078 A1 | * | 8/2012 | Stanley ................... | A61B 1/05 600/109 |
| 2012/0289975 A1 | * | 11/2012 | Martin ................ | A61B 17/062 606/147 |
| 2014/0128671 A1 | * | 5/2014 | Riek ...................... | A61B 1/018 600/104 |

OTHER PUBLICATIONS

Catarci, et al., Major and Minor Injuries During the Creation of Pneumoperitoneum, Surgical Endoscopy, 2001, 15 (6):566-569.

FDA, Laparoscopic Trocar Injuries: A Report from a U.S. Food and Drug Administration (FDA) Center for Devices and Radiological Health (CDRH) Systematic Technology Assessment of Medical Products (STAMP) Committee: FDA Safety Communication, Nov. 7, 2003, 16 pages.

Jansen, et al., Complications of Laparoscopy: A Prospective Multicentre Observational Study, British Journal of Obstetrics and Gynaecology, 1997, 104:595-600.

Jansen, et al., Complications of Laparoscopy: An Inquiry About Closed- Versus Open-Entry Technique, American Journal of Obstetrics and Gynecology, 2004, 190:634-638.

Kasotakis, et al., Optimal Pressure of Abdominal Gas Insufflation for Bleeding Control in a Severe Swine Splenic Injury Model, Journal of Surgical Research, 2013, 184:931-936.

Magrina, Complications of Laparoscopic Surgery, Clinical Obstetrics & Gynecology, 2002, 45(2):469-480.

Molloy, et al., Laparoscopic Entry: A Literature Review and Analysis of Techniques and Complications of Primary Port Entry, Aust N Z J Obstet Gynaecol, 2002, 42(3):246-254.

Sava, et al., Abdominal Insufflation for Prevention of Exsanguination, Journal of Trauma, 2003, 54:590-594.

Schafer, et al., Trocar and Veress Needle Injuries During Laparoscopy, Surgical Endoscopy, 2001, 15(3):275-280.

Velmahos, et al., Abdominal Insufflation for Control of Bleeding After Severe Splenic Injury, Journal of Trauma, 2007, 63:285-290.

Velmahos, et al., Abdominal Insufflation Decreases Blood Loss Without Worsening the Inflammatory Response: Implications for Prehospital Control of Internal Bleeding, The American Surgeon, 2008, 74(4):297-301.

Vilos, Litigation of Laparoscopic Major Vessel Injuries in Canada, Journal of the American Association of Gynecologic Laparoscopists, 2000, 7(4):503-509.

Vilos, Laparoscopic Bowel Injuries: Forty Litigated Gynaecolgoical Cases in Canada, J. Obstet. Gynaecol. Can., 2002, 24(3):224-230.

Wikipedia, "Lean Startup", Last Modified on May 27, 2016, 11 pages.

Yuzpe, Pneumoperitoneum Needle and Trocar Injuries in Laparoscopy. A Survey on Possible Contributing Factors and Prevention, Journal of Reproductive Medicine, 1990, 35(5):485-490.

PCT International Search Report and Written Opinion, PCT/US2014/018621, dated May 19, 2014.

PCT International Preliminary Report on Patentability, PCT/US2014/018621, dated Sep. 1, 2015.

* cited by examiner

SYSTEMS FOR ABDOMINAL WALL LIFTING AND NEEDLE INSERTION

CROSS-REFERENCE TO RELATED APPLICATIONS

This application represents the national stage entry of PCT International Application No. PCT/US2014/018621 filed Feb. 26, 2014, which claims the benefit of U.S. Provisional Application Ser. No. 61/769,231 filed on Feb. 26, 2013, the disclosures of which are incorporated by reference here in their entirety for all purposes.

BACKGROUND OF THE INVENTION

The disclosure invention relates to systems and methods for diagnosing and treating internal injuries including organ bleeding. More particularly, the disclosure relates to systems and methods for diagnosing abdominal bleeding and performing abdominal insufflations.

Exsanguination is a major cause of death. A majority of injury-related deaths occur in the pre-clinical period due to intracavitary bleeding. Bleeding from the extremities can be controlled temporarily by simple methods, such as direct pressure, hemostatic dressings, or tourniquets. A variety of systems and methods have been developed to help keep blood loss to a minimum during the transport to the hospital or clinic and the initial evaluation.

However, for intracavitary bleeding, particularly in the abdomen, the systems and methods that apply to the extremities are generally unsuited. For example, it can be extremely difficult to identify the location of bleeding in the abdomen and, even ignoring this difficulty, can be difficult or impossible to apply a systems and methods such as tourniquets or even to apply pressure to the source of internal bleeding. However, abdominal gas insufflation (AGI) has been shown to be an effective method for temporary control of blood loss due to abdominal bleeding. During AGI, the abdominal cavity is insufflated with a gas (usually carbon dioxide) by using a hollow needle (for example, a Veress needle) connected to an insufflator.

To perform AGI, an assistant lifts the abdominal wall using penetrating clamps, while a surgeon inserts the hollow needle into the abdomen. The technique is limited by the need for two people to perform the procedure, the traumatic lifting of the abdominal wall, and the uncontrolled nature of the needle insertion. The latter limitation is controlled by insertion of the needle being performed by a skilled surgeon or similarly trained individual because failure to control the insertion may result in inadvertent injury to the organs or vessels, such as injury to the intestines, puncture of large blood vessels, both of which can further exacerbate internal bleeding, and the risk of infection. Over 50 percent of laparoscopic injuries to the gastrointestinal tract and major vessels occur during the initial entry phase.

As such, generally, AGI is performed only in clinical settings, where multiple individuals, including at least one highly-skilled/trained individual such as a surgeon, are available to performed AGI in a controlled and coordinated environment. Thus, though an effective means for controlling internal bleeding, AGI is generally not used in situations outside of the hospital or clinic. Thus, unlike injuries to the extremities that benefit from a wealth of systems and methods to control bleeding, intraperitoneal abdominal bleeding continues to be a challenge to control in any consistent manner in the field and prior to arriving at the clinic or hospital. Even once at the hospital or clinic, there are few systems and methods for controlling abdominal bleeding and, for those that exist such as AGI, it can be resource intensive.

Therefore, it would be desirable to have systems and methods for controlling abdominal bleeding in both a clinical/hospital setting and, more particularly, when the resources of a hospital or clinic are not available or are limited.

SUMMARY OF THE INVENTION

The present invention overcomes the aforementioned drawbacks by providing systems and methods for performing AGI that reduce the resources needed to perform the procedure and the potential challenges associated with performing AGI. In particular, the present disclosure provides systems and methods that allow a single individual to lift the abdominal wall up and away from the underlying intestines and blood vessels, creating a safer pathway for blind insertion of the needle, and insert the needle in a carefully controlled manner. The systems and methods also provide the ability to place the needle by a gradual and controlled insertion into the abdomen, and can even provide the user with feedback indicating proper insertion to protect against inadvertent over-insertion.

In accordance with one aspect of the present invention, a system is provided for guiding a needle into an abdomen of a subject. The system includes a clamping system including a first clamp arranged in opposition to a second clamp and configured to be moved between a first closed position and a second open position by actuating at least one handle. The system also includes a needle advancement control configured to receive a needle and advance the needle toward the first clamp and the second clamp to extend therebetween and into a portion of the abdomen of the subject when arranged between the first clamp and the second clamp. The system further includes a feedback device configured to monitor the needle as it is advanced into the portion of the abdomen of the subject and provide feedback indicating that the needle has pierced the portion the abdomen In accordance with another aspect of the present invention, a system is disclosed for delivering an insufflations gas to an abdomen of a patient. The system includes a clamp system configured to engage and lift an abdominal wall of a patient and including a needle guide path directing into the abdominal wall of the patient. The system also includes a needle arranged within the needle guide path and an insufflator coupled to the needle to deliver a gas along the needle and through the abdominal wall of the patient. The system further includes a needle control system configured to control advancement of the needle along the needle guide path and into the abdominal wall of the patient.

In accordance with yet another aspect of the present invention, a kit is provided for delivering an insufflations gas to an abdomen of a patient. The kit includes a diagnostic device configured to analyze the abdomen of the patient and provide feedback upon detecting a pool of blood and a clamp system configured to engage and lift an abdominal wall of a patient and including a needle guide path directing into the abdominal wall of the patient. The kit also includes a needle arranged within the needle guide path, an insufflator coupled to the needle to deliver a gas along the needle and through the abdominal wall of the patient, and a needle control system configured to control advancement of the needle along the needle guide path and into the abdominal wall of the patient.

The foregoing and other aspects and advantages of the invention will appear from the following description. In the description, reference is made to the accompanying drawings that form a part hereof, and in which there is shown by way of illustration a preferred embodiment of the invention. Such embodiment does not necessarily represent the full scope of the invention, however, and reference is made therefore to the claims and herein for interpreting the scope of the invention.

BRIEF DESCRIPTION OF THE DRAWINGS

FIGS. 8A and B are a perspective views of the control system of FIG. 6 with configurations of insufflators in accordance with the present invention coupled therewith.

DETAILED DESCRIPTION OF THE INVENTION

Figure 1:
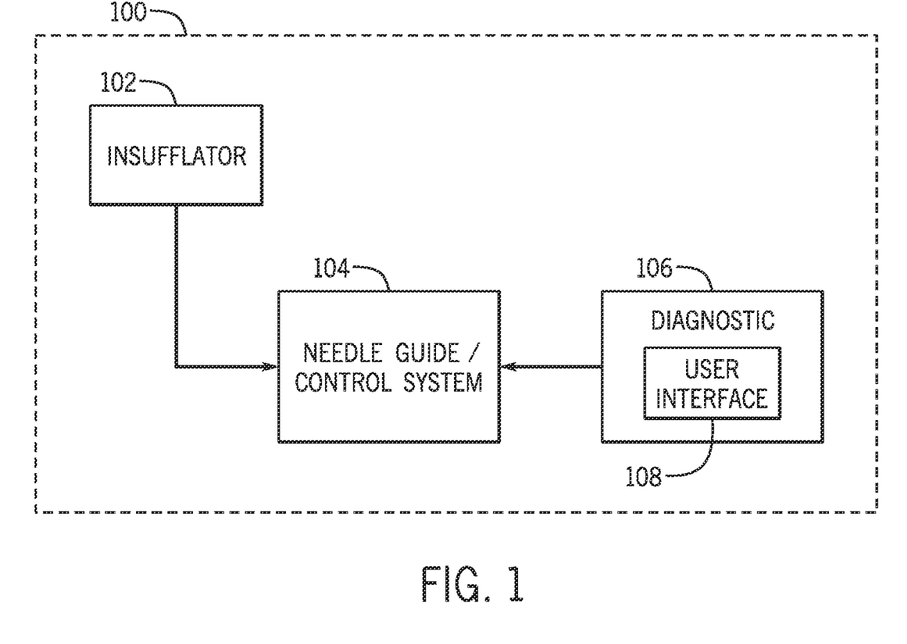
FIG. 1 is a schematic diagram of an example of a diagnostic, control, and insufflation system in accordance with the present invention.

Referring now to FIG. 1, a schematic diagram of an example of a system 100 in accordance with the present invention is shown. The system 100 may be organized as a kit for a medical technician, such as a doctor, EMT, firefighter, or paramedic, to keep in an emergency medical service vehicle or at a hospital. The system may include an insufflator 102, a needle guide/control system 104, and a diagnostic device 106 with a user interface 108. The insufflator may contain any appropriate gas for the insufflation. Carbon dioxide is commonly used because it is known to readily diffuse in the body. However, other gases may be used. As will be described, the needle guide/control system 104 may take various forms and be used by the medical technician to control the insertion of the needle into the abdomen. The diagnostic device 106 with the user interface 108 may be used by the medical technician to determine whether a subject has internal bleeding in the abdomen. For example, the diagnostic device 106 may be an ultrasound device that is, for example, specifically designed to identify pooled liquid, such as pooled blood from internal bleeding within the abdomen. That is, the diagnostic device 106 may be configured to deliver ultrasound waves into the abdomen of the patient and receive waves in response to the delivery of the ultrasound waves to detect the pool of blood. To this end, the user interface 108 may be a display or, in some instances, may be as simplified interface designed for field use. That is, the user interface may be a light, sound, or other alert mechanism that changes states upon determining that a pool of liquid has been identified.

Figure 2:
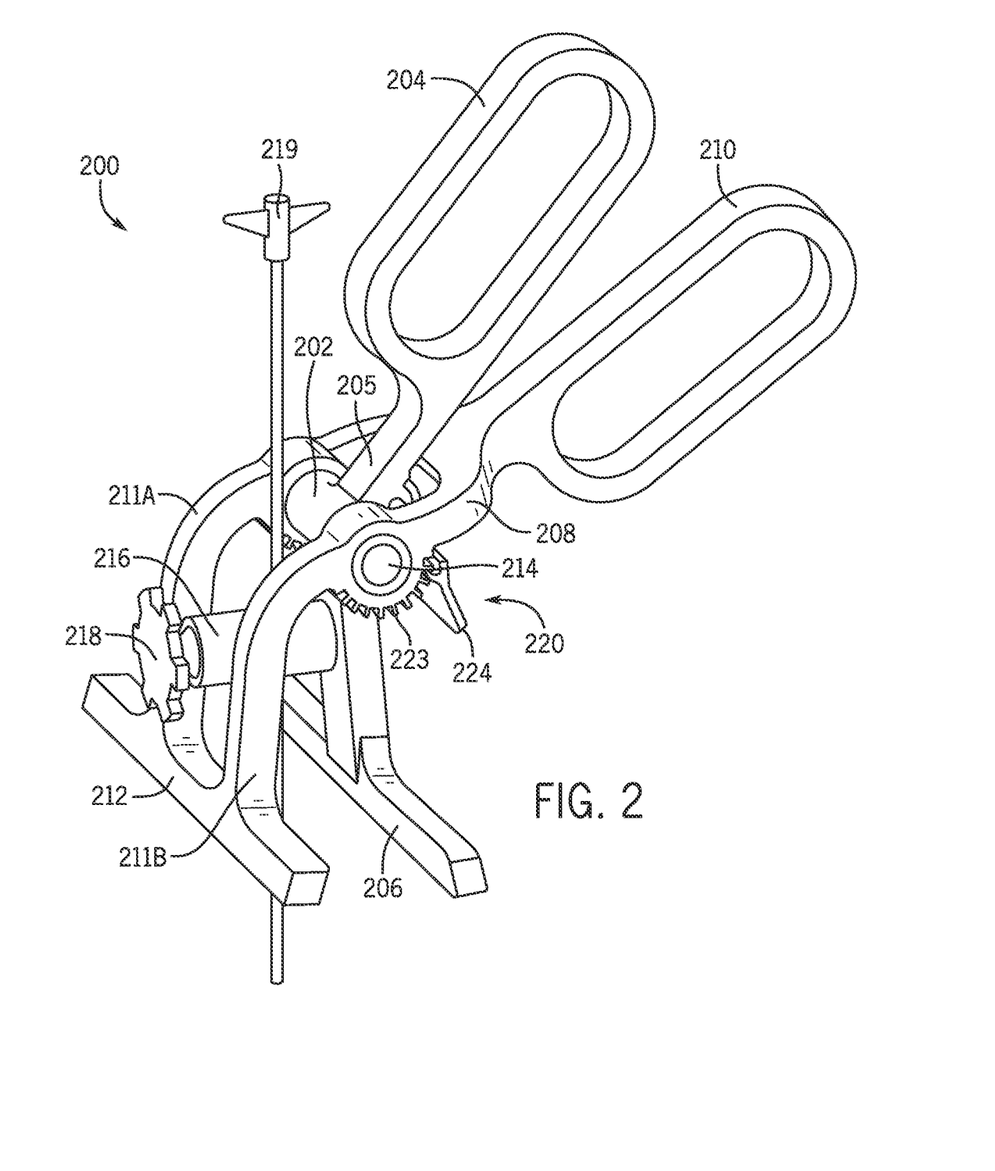
FIG. 2 is a perspective view of a configuration of a control system in accordance with the present invention.

Referring now to FIG. 2, a perspective view of a configuration of a clamping or control system 200 in accordance with the present invention is shown. The system 200 includes a first lever 202 having a handle 204 at a first end, a shaft 205 extending from the handle 204, and a clamp 206 at the second end. The system 200 includes a second lever 208 having a handle 210 at a first end, a shaft that is divided into two portions 211A and 211B extending from the handle 210, and a clamp 212. A fulcrum or a hinge 214 pivotably connects the first lever 202 and the second lever 208. In this way, the clamps 206, 212 act to open and close in a jaw action. Thus, the two portions 211A, 211B can be referred to a jaw member that moves relative to another jaw member represented by the first lever 202.

The system 200 also includes a needle advancement control 216. In the illustrated configuration, the needle advancement control 216 may be mounted to the shaft 205 of the first lever 202. However, the needle advancement control 216 may similarly be mounted or coupled to other portions of the system 200 that permit a single user to position the system 200 to engage an abdomen of a patient, lift the abdomen with the system, and extend a needle 219 into the lifted portion of the abdomen. The needle advancement control 216 may include a user interface or needle driver 218 and a needle guide path (obscured in FIG. 2) for a needle 219, collectively referred to as an actuation device or mechanism.

As described, the first lever 202 is pivotally connected to the second lever 208 by way of the hinge 214. The first lever 202 may be removably connectable to the second lever 208, or the first lever 202 may be fixedly attached to the second lever 208. In either case, the clamp 206 of the first lever 202 is capable of being moved toward and away from the clamp 212 of the second lever 208 to either grab or release an abdominal wall of a patient.

In the illustrated configuration, the two shaft portions 211A and 211B of the second lever 208 are arranged to be on either side of the shaft 205 of the first lever 202 so that the first lever 202 and the second lever 208 are able to move freely without obstructing each other. In the illustrated configuration, the clamp 206 of the first lever 202 and the clamp 212 of the second lever 208 are formed as single bars that are substantially aligned so they may clamp together to lift an abdominal wall of a patient.

In the illustrated configuration, the hinge 214 may includes a lock 220 that includes teeth 223 and a plate 224 that engages with and locks with the teeth 223. The lock 220 may be used to lock to the first lever 202 and the second lever 208 in position by pushing the locking plate 224 into the teeth-like ridges 223.

The needle advancement control 216 may have one or more needle guide paths (obscured in FIG. 2) for receiving the needle 219. When coupled with the needle 219, the needle advancement control 216 may be used to advance or retract the needle 219 in a highly-controlled or incremental manner, as will be further described. That is, advancement of the needle 219 may be performed by turning the needle driver 218, which, in turn, moves the needle a controlled increment toward or away from the clamps 212, 216. In this way, rotational movement is translated into a controlled linear movement of the needle. For example, turning the needle driver 218 in a single rotation may advance or retract the needle 219 by, for example, one centimeter.

As will be described further, it is contemplated that the needle 219 may be a Veress needle. A Veress needle is a hollow needle with a beveled needle point and a spring-loaded stylet at one end. The spring-loaded stylet extends out of the beveled needle point such that when the Veress needle pressed against a patient, the spring-loaded stylet compresses back into the hollow Veress needle, exposing the beveled needle point. When the beveled needle point has broken through a patient's abdomen, the spring-loaded stylet springs back out of the hollow Veress needle, indicating to the medical technician that there is no need to push the needle in any further. To a trained person, such as a surgeon, this feedback can be sufficient. However, to an untrained or less-skilled individual or in a non-clinical or field environment, this feedback can be readily overlooked. Thus, as will be described, the above-described and other systems and methods may utilize additional systems to provide feedback that the Veress or other needle has penetrated the abdomen and protect against further insertion once the needle has penetrated the abdomen.

Figure 3:
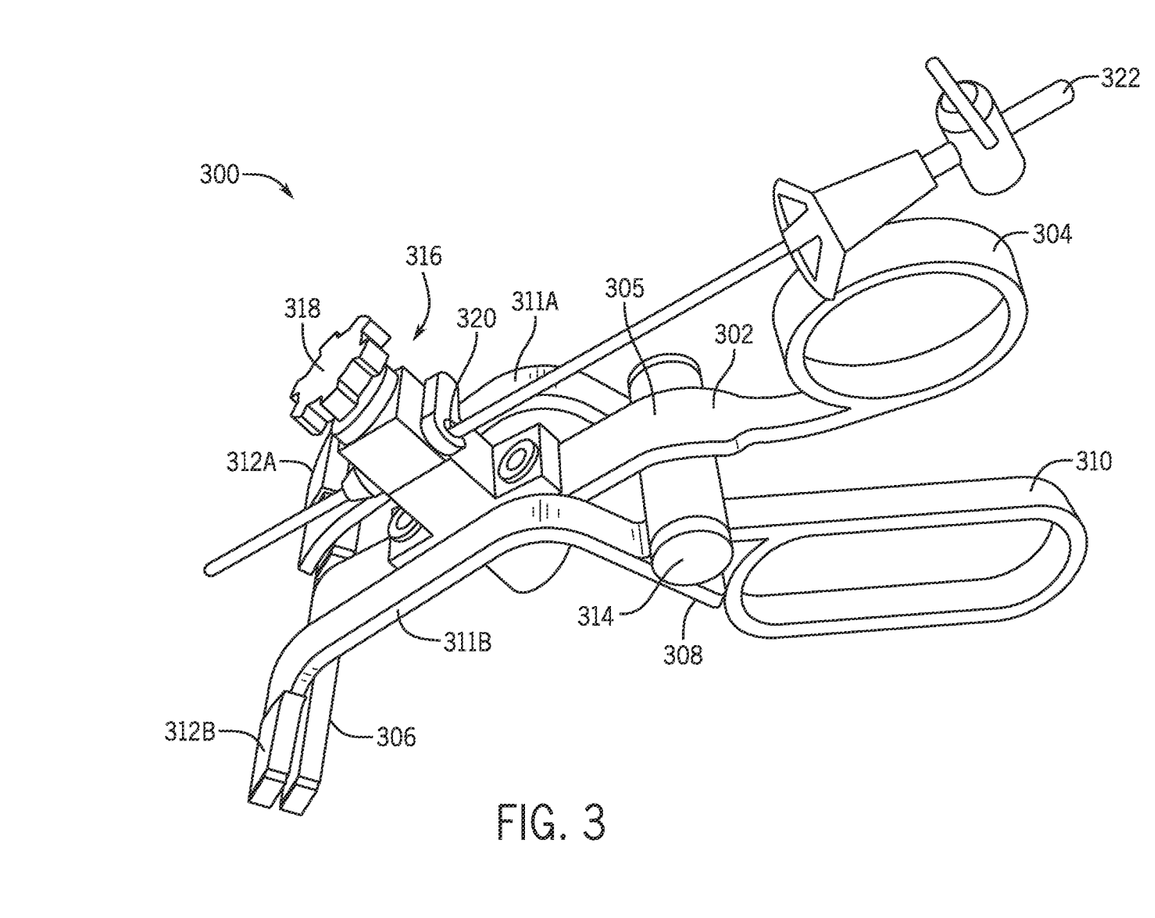
FIG. 3 is a perspective view of a configuration of another control system in accordance with the present invention.

Referring now to FIG. 3, a perspective view of another clamping or control system 300 is shown. The system 300 includes a first lever 302 having a handle 304, a shaft 305, and a clamp end 306. The system 300 also includes a second lever 308 having a handle 310, a shaft that may again include two shaft portions 311A and 311B, and a clamp that may include two clamping ends 312A and 312B. A fulcrum or a hinge 314 connects the first lever 302 and second lever 308. Again, this arrangement can be referred to as providing a jaw function.

A needle advancement control 316 is provided that includes a needle driver 318 and a needle guide path 320 for receiving a needle 322. Collective the needle driver 318 and needle guide path 320 may be referred to as an actuation mechanism or device. The first lever 302 is pivotally connected to the second lever 308 by way of the hinge 314. The first lever 302 may be removably connectable to the second lever 308, or the first lever 302 may be fixedly attached to the second lever 308. In either case, the clamp 306 of the first lever 302 is capable of being moved toward and away from the clamp 312 of the second lever 308 about the hinge 314 to either grab or release the abdominal wall of a patient. The two shaft portions 311A and 311B of the second lever 308 are arranged to be on either side of the shaft 305 of the first lever 302 so that the first lever 302 and the second lever 308 are able to move freely without obstructing each other. The clamp 306 of the first lever 302 may be a single bar that is substantially aligned with the clamps 312A and 312B of the second lever 308 so they may clamp together to lift an abdominal wall of a patient.

The needle advancement control 316 may have one or more needle guide paths 320 for driving the needle 322 into a patient's abdomen. The needle advancement control 316 may be used to control insertion of the needle 322 into the patient's abdomen in a highly-controlled or incremental fashion. The advancement of the needle 322 may be performed by turning the needle driver 318 to guide the needle 322 through the needle guide path 320 and into the patient's abdomen. As described, the needle 322 may be a Veress needle.

Figure 4:
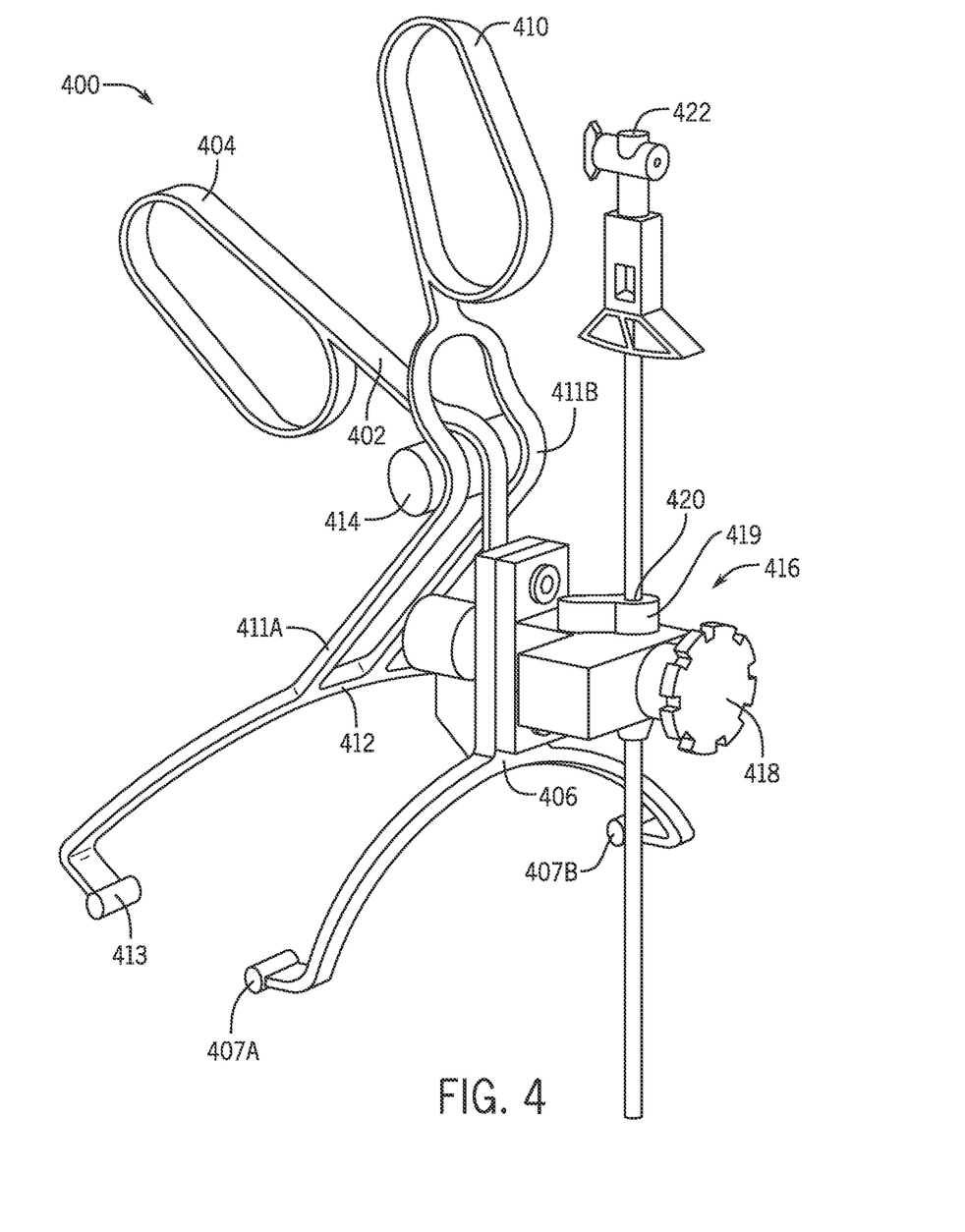
FIG. 4 is a perspective view of a configuration of yet another control system in accordance with the present invention.

Referring now to FIG. 4, a perspective view of another clamping or control system 400 is shown. The system 400 includes a first lever 402 having a handle 404, a shaft 405, and a clamp 406, which may have two prongs 407A and 407B. The system 400 also includes a second lever 408 having a handle 410, a shaft that may be formed of two shaft portions 411A and 411B, and a clamp 412 having two prongs 413 (the second prong is obscured in FIG. 4). A fulcrum or hinge 414 pivotably connects the first and second lever 402, 408. This configuration can be described as providing a jaw function.

An actuation mechanism may include a needle advancement control 416 and a needle driver 418. Also, in the illustrated configuration, a locking mechanism 419 is provided for locking a needle 422 in place within a needle guide path 420 is provided. The first lever 402 is pivotally connected to the second lever 408 by way of hinge 414. The first lever 402 may be removably connectable to the second lever 408, or the first lever 402 may be fixedly attached to the second lever 408. In either case, the clamp 406 of the first lever 402 is capable of being moved toward and away from the clamp 412 of the second lever 408 to either grab or release the abdominal wall of a patient. The two shafts 411A and 411B of the second lever 408 are arranged to be on either side of the shaft 405 of the first lever 402 so that the first lever 402 and the second lever 408 are able to move freely without obstructing each other. The clamp 406 of the first lever 402 and the clamp end 412 of the second lever 408 are U-shaped bars with prongs 407A, 407B, and 413 that are substantially aligned so they may clamp together to lift an abdominal wall of a patient.

The needle advancement control 416 may have one or more needle guide paths 420 for driving the needle 422 into a patient's abdomen. The needle advancement control 416 may be used for a controlled insertion of the needle 422 into the patient's abdomen. The advancement of the needle 422 may be performed by turning the needle driver 418 to guide the needle 422 through the needle guide path 420 and into the patient's abdomen. The needle 422 being inserted into a patient's abdomen may be a Veress needle.

Figure 5:
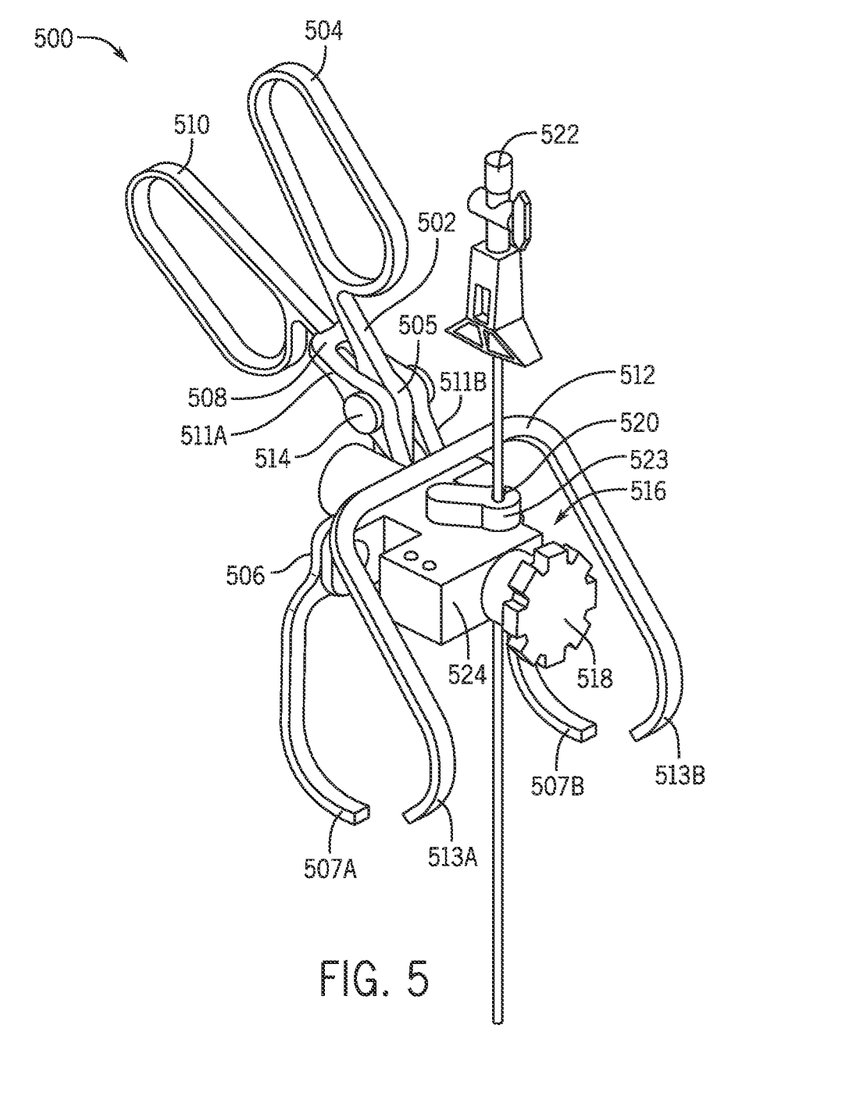
FIG. 5 is a perspective view of a configuration of a needle driver in accordance with the present invention.

Referring now to FIG. 5, a perspective view of another configuration 500 of the present invention is shown. The system 500 includes a first lever 502 having a handle 504, a shaft 505, and a clamp 506 having two prongs 507A and 507B. The system 500 also includes a second lever 508 having a handle 510, two shaft portions 511A and 511B, and a clamp 512 having two prongs 513A and 513B. A fulcrum or a hinge 514 connects the levers 502, 508. The first lever 502 may be removably connectable to the second lever 508, or the first lever 502 may be fixedly attached to the second lever 508. In either case, the clamp 506 of the first lever 502 is capable of being moved toward and away from the clamp 512 of the second lever 508 to either grab or release the abdominal wall of a patient. The two shaft portions 511A and 511B of the second lever 508 are arranged to be on either side of the shaft portion 505 of the first lever 502 so that the first lever 502 and the second lever 508 are able to move freely without obstructing each other. The clamp 506 of the first lever 502 and the clamp 512 of the second lever 508 are U-shaped bars with prongs 507A, 507B, 513A, and 513B that are substantially aligned so they may clamp together to lift an abdominal wall of a patient. This may be described as providing a jaw function.

An actuation mechanism or a needle advancement control 516 is provided that includes a needle driver 518 and a needle guide path 520 for receiving a needle 522. A locking mechanism 523 and an electronic module 524 are also included. The needle advancement control 516 may have one or more needle guide paths 520 for driving the needle 522 into a patient's abdomen. The needle advancement control 516 may be used for a controlled insertion of the needle 522 into the patient's abdomen. The advancement of the needle 522 may be performed by turning the needle driver 518 to guide the needle 522 through the needle guide path 520 and into the patient's abdomen. The needle 522 being inserted into a patient's abdomen may be a Veress needle. The locking mechanism 523 may be used to lock the needle 522 in place. For example, the locking mechanism 523 may be used to lock a Veress needle in place when the Veress needle has been inserted into a patient's abdomen. The electronic module 524 may have two visual indicators, such as LEDs, for indicating when the needle 522 has entered into a patient's abdomen. The electronic module may also have an audio indicator outputting a sound to indicate when the needle 522 has entered a patient's abdomen. The electronic module may work with a Veress needle by indicating when the stylet is compressed and when the stylet is extended. This may be accomplished by having different LED colors to indicate the different positions of the stylet (for example, green for expanded and red for compressed) or outputting a sound when the stylet has extended or compressed (for example, outputting a sound when the stylet has expanded into a patient's abdomen).

Figure 6:
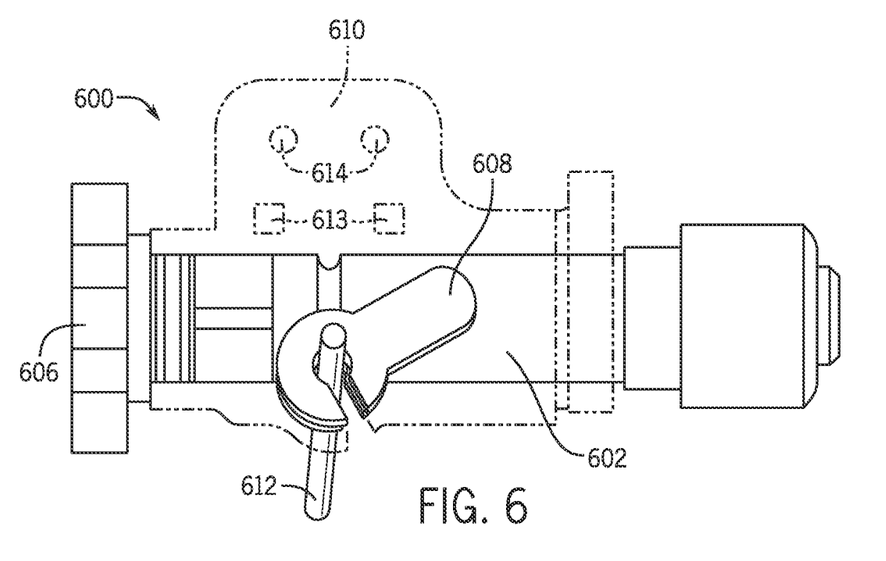
FIG. 6 is a perspective view of still another configuration of a control system in accordance with the present invention.
Figure 7:
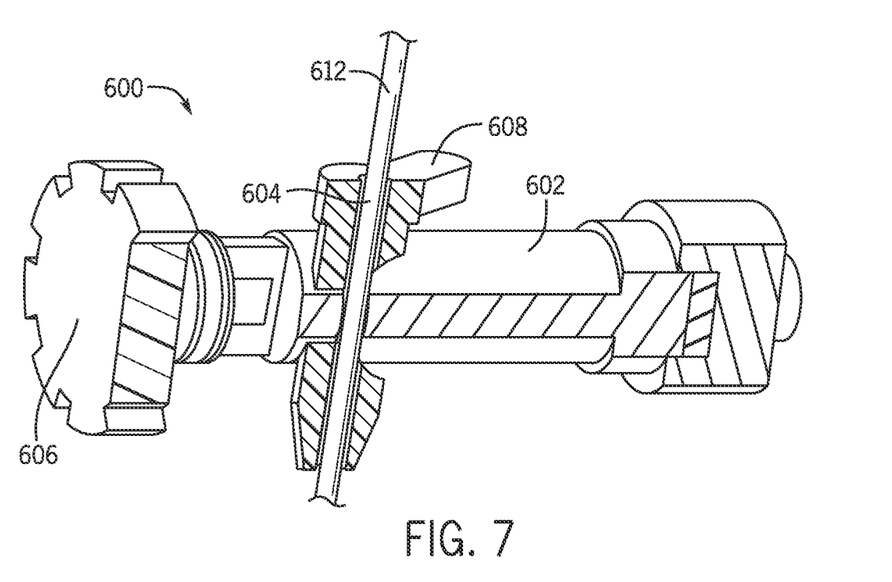
FIG. 7 is a perspective view of a configuration of a needle driver in accordance with the present invention.

Referring now to FIGS. 6 and 7, perspective views of a needle actuation mechanism or driver 600 are shown. The needle driver 600 includes a shaft 602, a needle guide path 604, a driving mechanism 606, a locking mechanism 608, and an electronic module 610. The shaft 602 may be used in mounting the needle driver 600 to a guide system as described above. The needle guide path 604 may be used to guide and advance or retract a needle 612 (for example, a Veress needle) into the abdomen of a patient. To this end, the driving mechanism 606 may be turned in either direction to drive the needle both toward and away from the patient in a controlled manner. The locking mechanism 608 may be used to lock the needle 612 in place. For example, the locking mechanism 608 may be used to lock a Veress needle in place after the Veress needle has been inserted into a patient's abdomen.

The electronic module 610 may include torque sensors 613 that detect the amount of torque being applied by the driving mechanism 606 to advance the needle 612. The shaft 602 is designed to be monitored by sensors 613. In one configuration, the sensors 613 may be strain gauges mounted to monitor the shaft 602, and coupled to the electronic module. During insertion, the tissue penetration resistance from the needle creates a torque that deforms the shaft area where two micro strain sensors are mounted. The sensors 613 record the shaft deformation considered to be in direct relation with the penetration resistance. Upon detecting a drop in the amount of torque applied, the sensors 613 provide feedback to one or more feedback devices 614, which may be designed to provide audio or visual feedback. That is, the sensors 613 may be configured to determine a change in the amount of torque being applied by the driving mechanism 606 to move the needle 612 and automatically provide an alert to the user via the feedback devices 614 to alert the user that the needle has penetrated the abdomen.

It is contemplated that the use of sensors 613 is one particularly sensitive way to determine penetration of the needle 612 into the abdomen and can sense when the needle has penetrated the abdomen when using the Veress or other needles. However, other systems are also possible. For example, as previously explained, the Veress needle has an inherent feedback mechanism created by the stylet automatically advancing from the compressed position after the needle penetrates the abdomen. As explained, a highly-trained individual will detect and recognize the subtle mechanical feedback transmitted along the needle when the stylet snaps back from the compressed position as a clear indication that the needle has penetrated the abdomen. However, if the individual is less trained or the environment, such as the field, obscures the subtle mechanical feedback, the individual may advance the needle too far. The present disclosure, in addition to or as an alternative to the torque sensor described above, may include a sensor configured to monitor for feedback indicative of the stylet of the Veress needle extending out from compressed position. Such mechanical or vibrational sensor can identify subtle mechanical feedback provided by the Veress needle and alert the user.

Thus, the above-described sensors may indicate to a user when to stop driving the needle into the patient. The sensors may be used with a Veress needle or other needles. The needle driver 600 may be used with multiple configurations of the present invention, but the needle driver 600 may be seen with the guide system of FIG. 5.

Figures 8A, 8B:
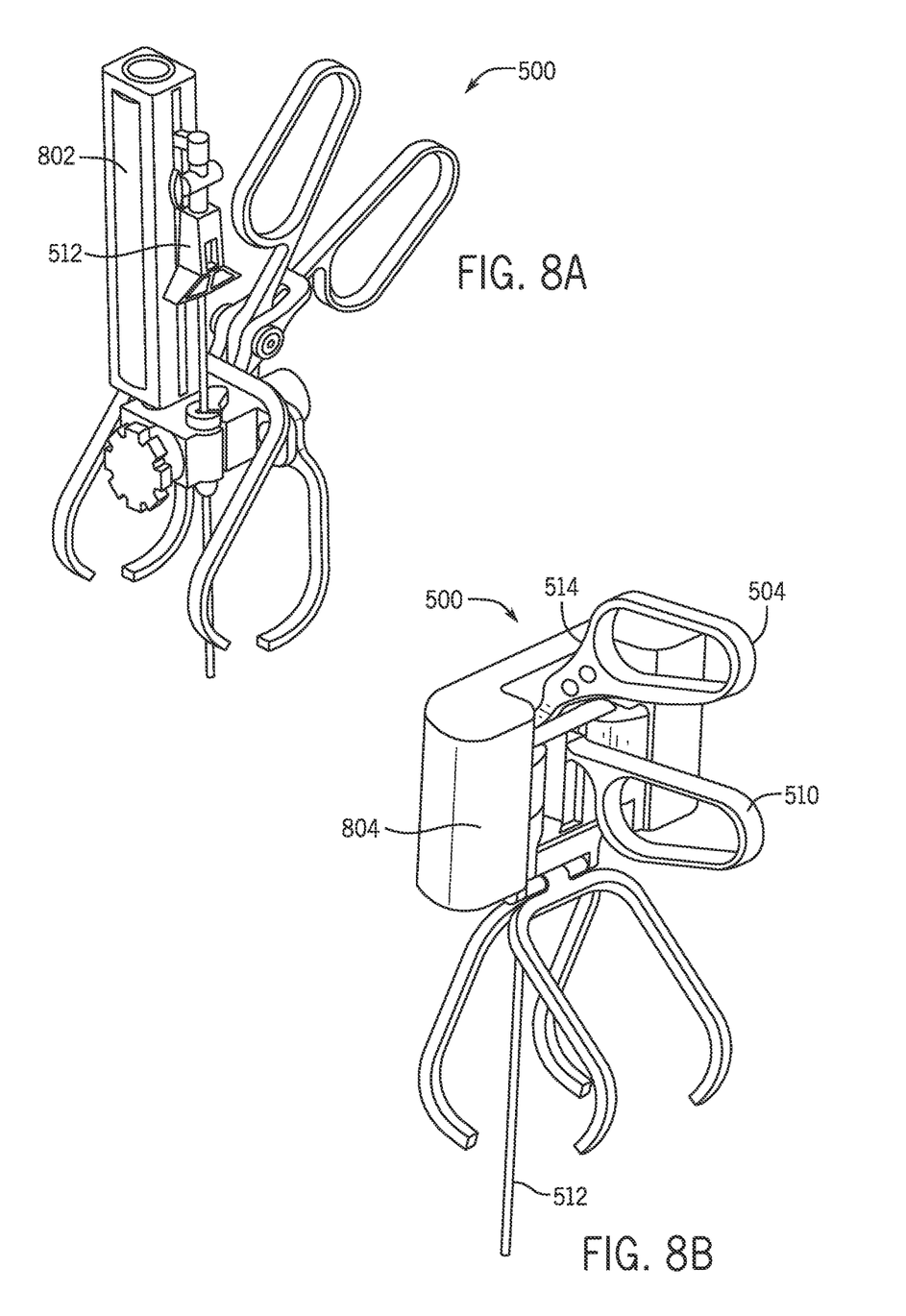

Referring now to FIGS. 8A and B, perspective views of systems 500 of FIG. 5 are shown being coupled with insufflators 802 and 804. Referring particularly to FIG. 8A, the insufflator 802 may be connected to the system 500 and also coupled to the needle 512 so the gas inside the insufflator 802 (for example, carbon dioxide) may be distributed to the needle and into a patient's abdomen to put pressure on any internal bleeding. Referring to FIG. 8B, the configuration of FIG. 5 may be modified for a different insufflator 804 design. The handles 504 and 510 may be placed at a different angle to accommodate the insufflator 804. In addition, the visual feedback devices 614 may be moved to the handle 504 so the user may better see the status of the location of the needle 522.

Figures 9A, 9B:
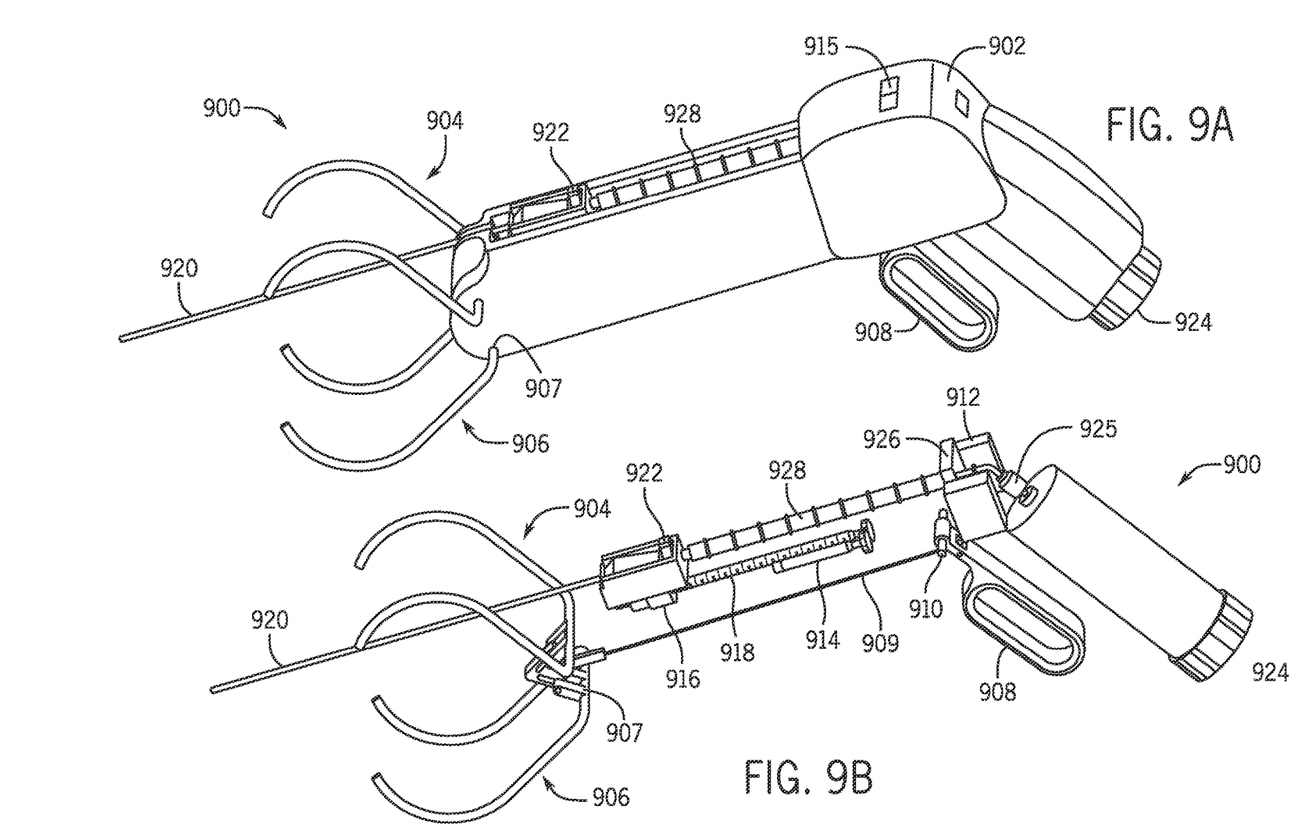
FIG. 9A is a perspective view of a configuration of a control and insufflations system in accordance with the present invention.
FIG. 9B is a perspective view of the system of FIG. 9A with a housing removed.

Referring now to FIGS. 9A and B, another system 900 is shown with and without a protective casing or housing 902 respectively. In this configuration, the above-described jaw function is achieved without levers. Rather, the system 900 includes first and second jaws 904, 906 connected to respective portions of a hinge 907. A single handle 908 is provided that opens and closes the jaws 904, 906 by actuating the hinge 907 using a linkage 909, which is illustrated as a mechanical linkage, but may also be electronic. In either case, the first jaw 904 and the second jaw 906 are coupled to the hinge 907 so that, when the handle 908 is pulled away from the first jaw 904 and second jaw 906, the first jaw 904 and the second jaw 906 move toward each other. In this manner, the first jaw 904 and the second jaw 906 may be used to lift the abdomen of a patient. This design is highly-effective at securing a portion of the abdomen and enables a clinician to quickly engage the abdomen and securely lift the abdomen and deliver a needle in a highly controlled manner, and even perform the desired insufflation procedure, all with a single hand.

A battery 910 is provided to power a programmable controller 912 and a motor 914. Power delivery from the battery 910 can be interrupted by use of an on/off switch 915. The system also includes a plurality of mechanical and electromechanical systems for controlling needle advancement, referred to as an actuation mechanism or device, and also for controlling insufflations. The systems may include a ball screw 916 and a ball screw nut 918, a needle 920, a locking mechanism 922, an insufflator 924, a solenoid valve 925, a flow sensor 926, and a flexible hose 928.

In operation, the battery 910 may power the programmable controller 912 and the motor 914. The on/off switch 915 may be used to trigger the motor 914 to move the needle 920 toward a patient whose abdominal wall has been lifted. The motor 914 may move the needle 920 toward a patient by twisting the ball screw 916 into the ball screw nut 918. In this way, the twisting, rotating motion is translated into a controlled linear movement of the needle. The motor 914 may be a stepper motor or other motor with a gearbox and a position encoder, and it may be controlled by the controller 912. After the needle 920 is in the desired position, the locking mechanism 922 may be used to lock the needle 920 in place. For example, the needle 920 may be locked in place when the needle 920 has been inserted into a patient. The needle 920 may be a Veress needle.

The patient's abdomen may be insufflated when the needle 920 has been inserted into the patient. The portable insufflator 924 includes a reservoir of compressed gas and is connected to the needle 920 via the flexible hose 928. The flow of gas may be controlled by the flow controller 926. The gas may be released by opening the solenoid valve 925. The gas may then flow through the flow sensor 926 and then into the flexible hose 928. The gas may then flow from the flexible hose 928 into the needle 920. If the needle 920 has been inserted properly into a patient, the gas may then flow through the needle 920 and into the patient. During needle insertion the flow of gas is low because tissues blocks the gas exit through the needle. Once the needle penetrates the abdominal wall, there will be an increase flow of gas registered by the flow sensor 926, and the programmable controller 912 will stop the motor and needle insertion, preventing internal organs injuries. This process may be used to insufflate the patient's abdomen.

The present invention has been described in terms of one or more preferred embodiments, and it should be appreciated that many equivalents, alternatives, variations, and modifications, aside from those expressly stated, are possible and within the scope of the invention.

What is claimed is:

1. A system for guiding a needle into an abdomen of a subject, the system comprising:
    a clamping system including a first clamp arranged in opposition to a second clamp, the first clamp and second clamp being rotatably coupled to a hinge and rotatable about the hinge between a first closed position and a second open position by rotating at least one handle about the hinge;
    a needle advancement control configured to receive a needle and advance the needle toward the first clamp and the second clamp to extend therebetween and into a portion of the abdomen of the subject when arranged between the first clamp and the second clamp; and
    a feedback device configured to monitor the needle as it is advanced into the portion of the abdomen of the subject and provide feedback indicating that the needle has pierced the portion the abdomen.

2. The system of claim 1 wherein the feedback device includes at least one of an auditory and a visual feedback indicator.

3. The system of claim 1 wherein the feedback device includes a sensor configured to monitor at least one of the needle advancement control and needle to determine when the needle has pierced the portion of abdomen.

4. The system of claim 3 wherein the sensor includes a torque sensor configured to monitor a torque associated with the needle advancement control to advance the needle.

5. The system of claim 1 wherein the needle advancement control device further comprises:
    a needle guide path; and
    an actuation device for driving the needle through the needle guide path.

6. The system of claim 5 further comprising a locking mechanism configured to lock the needle relative to the guide path.

7. The system of claim 1 further comprising a motor configured to advance and retract the needle relative to the first and second clamp.

8. The system of claim 1 further comprising an insufflations source configured to be coupled to the needle to deliver a gas to the abdomen of the subject through the needle.

9. The system of claim 1 wherein the needle control system includes a controller programmed to coordinate advancement of the needle along the needle guide path and delivery of the gas through the needle.

10. A system for delivering an insufflations gas to an abdomen of a patient, the system comprising:
    a clamp system configured to engage and lift an abdominal wall of a patient, the clamp system including a first clamp and a second clamp opposing the first clamp to engage opposing sides of the abdominal wall of a patient, the first clamp and second clamp coupled to one another and rotatable about a common axis, the first clamp having a first handle and the second clamp having a second handle, the first handle and the second handle rotatable about the common axis to move the first clamp and the second clamp between a first closed position and a second open position, the clamp system including a needle guide path directing into the abdominal wall of the patient;
    a needle arranged within the needle guide path;
    an insufflator coupled to the needle to deliver a gas along the needle and through the abdominal wall of the patient; and
    a needle control system configured to control advancement of the needle along the needle guide path and into the abdomen wall of the patient.

11. The system of claim 10 wherein the needle advancement system translates rotational movement into linear advancement of the needle along the needle guide path.

12. The system of claim 10 wherein the needle advancement system includes a motor configured to drive the needle along the needle guide path.

13. The system of claim 10 further comprising a single handle system configured to cause the needle control system to advance the needle and delivery of the gas from the insufflator.

14. The system of claim 10 further comprising at least one sensor configured to monitor at least one of the needle control system and the needle to determine when the needle has pierced the abdomen wall.

15. The system of claim 14 wherein the at least one sensor includes a torque sensor.

16. The system of claim 10 wherein the clamp system includes jaws pivotally connected to move between a closed position and an open position using a single hand.

17. A kit for delivering an insufflations gas to an abdomen of a patient, the kit comprising:
    a diagnostic device configured to analyze the abdomen of the patient and provide feedback upon detecting a pool of blood;
    a clamp system having two opposing clamps coupled to a hinge that are configured to engage and lift an abdominal wall of a patient by angularly displacing a handle about the hinge, the handle being coupled to one of the two opposing clamps, the clamp system further including a needle guide path directing into the abdominal wall of the patient;
    a needle arranged within the needle guide path;
    an insufflator coupled to the needle to deliver a gas along the needle and through the abdominal wall of the patient; and a needle control system configured to control advancement of the needle along the needle guide path and into the abdominal wall of the patient.

18. The kit of claim 17, wherein the diagnostic device is configured to deliver ultrasound waves into the abdomen of the patient and receive waves in response to the delivery of the ultrasound waves to detect the pool of blood.

19. The kit of claim 17 further comprising a single handle configured to control the clamp system, insufflator, and needle control system.

20. The kit of claim 17 further comprising at least one sensor configured to monitor at least one of the needle control system and the needle to detect indications that the needle has penetrated the abdominal wall of the patient and a controller configured to coordinate operation of the clamp system, needle control system, and insufflator.

21. A system for guiding a needle into an abdomen of a subject, the system comprising:
    a clamping system including a first lever and a second lever rotatable about a pivot pin to move a first clamp and a second clamp between a first closed position and a second open position, the pivot pin extending transversely across the first lever and the second lever, wherein the first lever is formed with a first handle and the first clamp and the second lever is formed with a second handle and the second clamp opposing the first clamp;
    a needle advancement control configured to receive a needle and advance the needle toward the first clamp and the second clamp to extend therebetween and into a portion of the abdomen of the subject when arranged between the first clamp and the second clamp; and
    a feedback device configured to monitor the needle as it is advanced into the portion of the abdomen of the subject and provide feedback indicating that the needle has pierced the portion of the abdomen.

22. The system of claim 21, wherein the pivot pin extends transversely across the first lever between the first handle and the first clamp and across the second lever between the second handle and the second clamp.

23. The system of claim 21, wherein a plurality of teeth are formed in the first lever and the second lever, the plurality of teeth being spaced apart to receive a plate that engages and locks with the teeth to secure the first lever and the second lever in the second open position.

24. The system of claim 21, wherein the needle advancement control is coupled to at least one of the first lever and the second lever at a location between one of the first handle and the second handle and the first clamp and the second clamp.

25. The system of claim 21, wherein the first handle is defined by a first elongate opening extending through the first lever and the second handle is defined by a second elongate opening extending through the second lever.

* * * * *